United States Patent [19]

Maddison et al.

[11] Patent Number: 4,798,206

[45] Date of Patent: Jan. 17, 1989

[54] IMPLANTED MEDICAL SYSTEM INCLUDING A SELF-POWERED SENSING SYSTEM

[75] Inventors: David S. Maddison, Wollstonecraft; Michael Skalsky, Waverley; Zoran Milijasevic, Elanora Heights; Stephen G. Perry, Gisborne; Loraine K. Holley, Rockdale; Gerhard R. Gotthardt, Castle Hill; Garry T. Richardson, Carlingford, all of Australia

[73] Assignee: Telectronics N.V., Curacao, Netherlands Antilles

[21] Appl. No.: 923,875

[22] Filed: Oct. 28, 1986

[51] Int. Cl.⁴ .............................................. A61N 1/36
[52] U.S. Cl. .................................. 128/419 P; 128/784
[58] Field of Search ............. 128/721, 722, 774, 782, 128/784–786, 419 P, 419 PG, 419 PS

[56] References Cited

U.S. PATENT DOCUMENTS 4,600,017 7/1986 Schroeppel ...................... 128/784

Primary Examiner—Max Hindenburg
Attorney, Agent, or Firm—Klaas & Law

[57] ABSTRACT

Self-contained, self-powered, flexible electrical control signal generating means are located in the right ventricle of a heart and generate electrical control signals solely by mechanical movements caused by actions of and conditions in the heart without any electrical connection to and supply of electrical energy from any other power source which electric control signals are transmitted to a control circuit system of an implanted control unit which control unit transmits an electrical signal to a stimulation electrode implanted in tissue at the apex of the right ventricle of the heart which stimulation electrode uses the electrical signal to stimulate the heart.

28 Claims, 16 Drawing Sheets

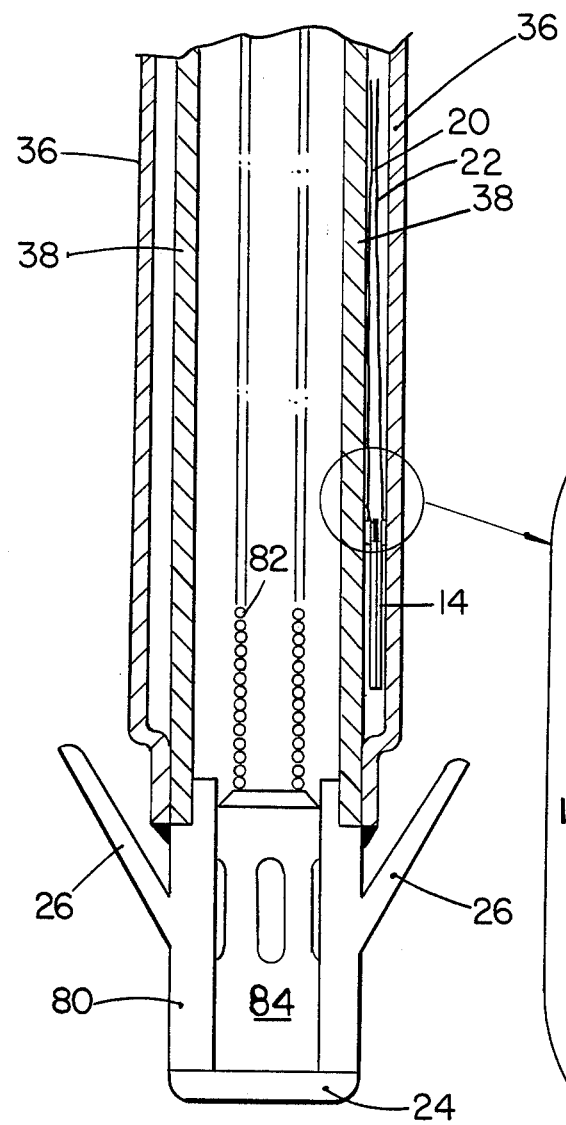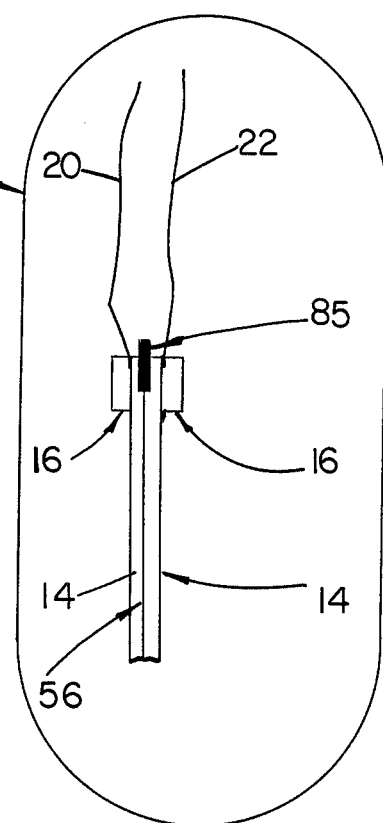
FIGURE 9
FIGURE 9a

FIGURE II

IMPLANTED MEDICAL SYSTEM INCLUDING A SELF-POWERED SENSING SYSTEM

FIELD OF THE INVENTION

This invention relates generally to an implanted medical system including a self-powered sensing system for use in obtaining information relative to the operation of a portion of a human body and to correlate such information with the operation of the medical system implanted in a portion of a human body, such as a heart pacemaker, and more particularly to a self-powered sensing system which can readily be used in close relationship with a stimulation electrode of a heart pacemaker.

BACKGROUND OF THE INVENTION

Heart pacemaker systems have been operating on the basis of detecting the electrical activity of the heart and adjusting the pulse generator output accordingly. More sophisticated pacemaker systems require that more information is obtained about the status of the heart, particularly in relation to the mechanical/hemodynamic activity, to more accurately simulate a natural, non-diseased heart. Sophisticated pacemaker systems are required to pace at different rates, determine the minimum amount of energy required to stimulate the heart and to provide back-up physiologic information to supplement the sensed electrical signal.

One way to minimize energy consumption of a pacing system is to use pulse energies that are as close as possible to actual tissue stimulation threshold requirements. To make a pacemaker system that can automatically adjust the pulse energy output necessitates the determination of the automatic stimulation threshold. This has been difficult to achieve as the measurement of the heart evoked potential following a pacemaker stimulus cannot be detected reliably due to electrical charge build up around the stimulating electrode immediately after pulse delivery. An alternate method to detect the heart capture is by a sensor that detects the mechanical/hemodynamic changes in the heart associated with a heart contraction.

Artificial Implantable Defibrillators (AID) also require the sensing of the hemodynamic state of the heart as electrical sensing alone may not be sufficiently reliable to distinguish between fibrillation and tachycardia.

Transducers for measuring various physical or chemical parameters from the heart, or other parts of the body, have long been a goal of pacemaker system designers. Up until now, these transducers have been affected by poor reliability and a great deal of complexity. Transducers to measure pressure within the body are known to the art from U.S. Pat. No. 4,023,562 Hynecek et al, which is incorporated herein by reference, but are typically only used acutely, such as for temporary diagnostic purposes.

A successful sensor should have the following requirements: sufficient stability to give useful measurements over the life-span of the heart pacemaker system; a size small enough to be compatible with the heart pacemaker system and also have minimal power consumption; packaging of the sensor in such a way that toxicity or other undesirable effects such as thrombosis or mechanical limitation are avoided; compatibility with the rest of the hardware system; an output signal which can be readily processed by the pacemaker's software system (where fitted); and an output signal which provides useful physiological data.

One attempt which has been made at producing a sensor which produces hemodynamic data in the form of pressure information and which meets some of these requirements is disclosed in U.S. Pat. No. 4,485,813 to Anderson et al., the disclosure of which is incorporated herein by reference. In this design a piezoelectric ceramic is used to convert pressure and motion into electrical signals. This design has the disadvantage that it required power from the pulse generator to make it function.

BRIEF DESCRIPTION OF THE INVENTION

This invention provides a sensing system which converts a force produced by a portion of a human body into an electrical signal which is used to provide information relating to the operation of that portion of the human body to an implanted medical device. The sensing system of this invention requires no outside electrical power and functions solely in response to the force applied by the human body to produce the electrical signal. When the sensing system has been implanted into the heart, the force can be from a heart motion or an altered hemodynamic state.

In one embodiment of the invention, a quantity of material, which is either piezoelectric or piezoresistive, is used to generate a voltage signal that is related to heart motion or an altered hemodynamic state. The quantity of material comprises a poly(vinylidene fluoride) (PVDF) film which has been specially processed to provide it with the desired piezoelectric characteristics. This quantity of material is very efficient at detecting the dynamic behavior of the heart, such as the stroke volume, pressure, contractility, valve closure, force of contraction and other hemodynamic indicators of heart activity. Also, this quantity of material does not require any power from an implanted medical system or any other device to accomplish its function. While the invention is particularly described in a functional relationship with a heart pacemaker system, it is understood that the invention may be used to generate an electric signal for use with any implanted medical system.

A sensing system used in conjunction with an implantable heart pacemaker system for control of the operation of the heart would include a control unit mounted in the body in a location remote from the heart. An electronic control circuit is associated with the control unit for controlling the operation thereof. A battery is included for supplying electrical energy to the control unit and to the electronic control circuit. A flexible lead mounted in the body extends between and is connected to the control unit and a stimulation electrode in the right ventricle of the heart for transmitting an electric signal from the control unit through the flexible lead to the stimulation electrode to be applied to the heart. The sensing system includes a sensing means comprising self-contained, self-powered, flexible, electrical signal generating means mounted in a portion of the flexible lead and located in the heart in spaced relationship to the stimulation electrode. The sensing means generates electrical control signals solely by mechanical movements induced solely by flexible movements of the flexible lead in the heart caused by action of and conditions in the heart and functions without any electrical connection to and supply of electrical energy from any other power source. The electrical control signals generated by the self-contained, self-powered, flexible, electrical signal generating sensing means are transmitted by suitable electrical transmitting means to the electronic control circuit means.

It is an object of this invention to provide a sensing system for use with an implanted medical system which sensing system is self-powered and generates electric control signals in response to a force applied thereto by the operation of a part of the human body and transmits the electrical control signals to the implanted medical system for use in controlling the operation thereof and which sensing system requires no electrical power from any other source to accomplish its functions.

It is another object of the invention to utilize a quantity of material, which is either piezoelectric or piezoresistive, to generate a voltage signal that is related to heart motion or an altered hemodynamic state.

Additional objects, advantages, and novel features of the invention are set forth in part in the description which follows which will be understood by those skilled in the art upon examination of the following or may be learned by practice of the invention. The objects and advantages of the invention may be realized and obtained by means of the instrumentalities and combinations particularly pointed out in the appended claims.

BRIEF DESCRIPTION OF THE DRAWINGS

FIG. 9 is a view with parts in section of a portion of a sensing system and a tip of a heart pacemaker;

FIG. 9a is an enlargement of a portion of the circled area of FIG. 9;

DESCRIPTION OF THE INVENTION

Figure 1:
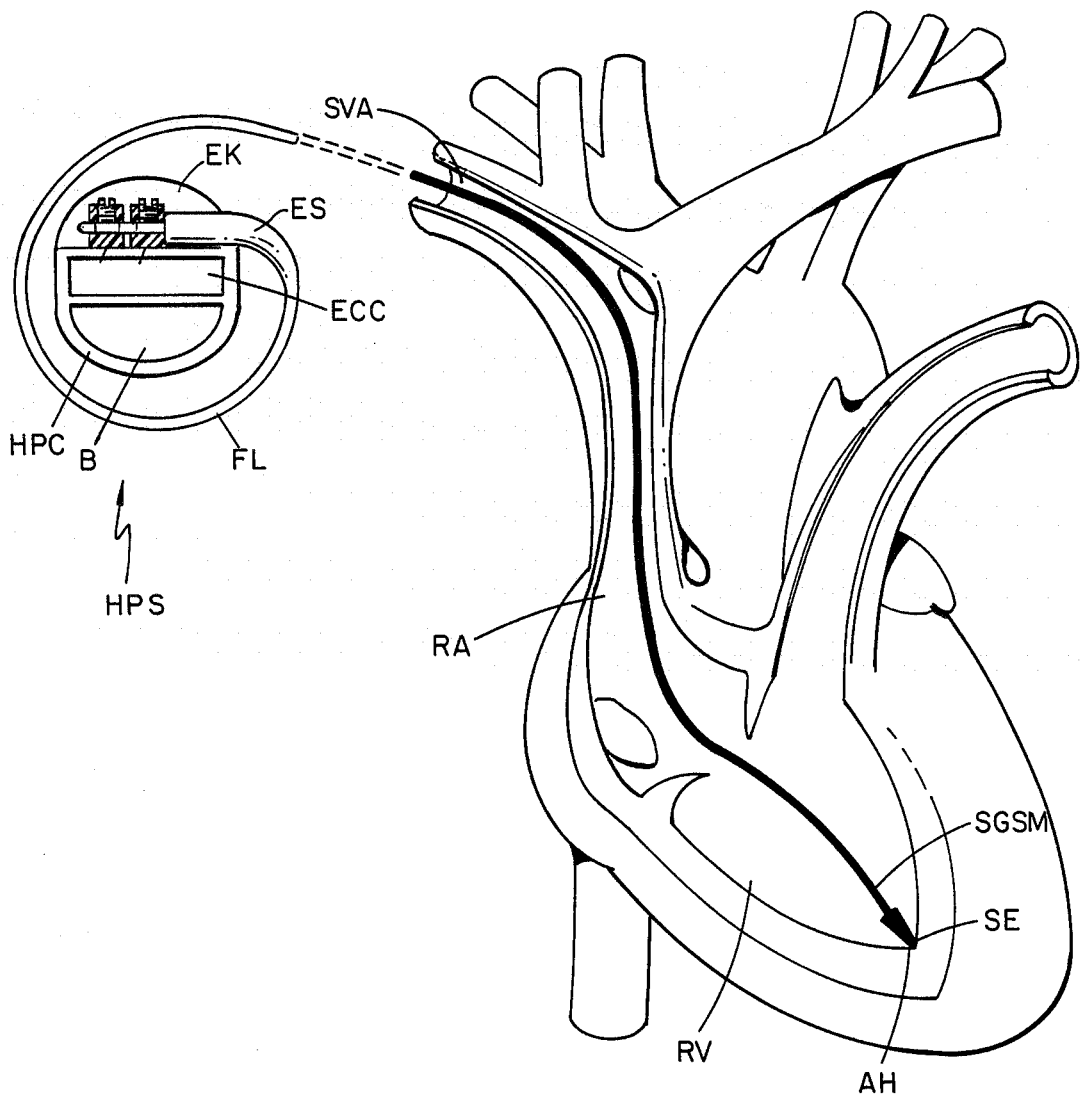
FIG. 1 is a schematic illustration of a heart showing the position of a portion of the sensing system in the right ventricle.

In FIG. 1, there is illustrated a sensing system of this invention in use with a heart pacemaker system HPS having a heart pacemaker control unit HPC containing a power supply B, an electronic control circuit ECC and a bipolar electrical connector EK. A bipolar electrical plug ES of a flexible lead FL is attached to the electrical connector EK. The flexible lead extends via the superior vena cava SVA into the right auricle RA and then into the right ventricle RV and is attached to a stimulation electrode SE which is secured in a conventional manner to the heart tissue at the apex of the heart AH. The signal generating sensing means SGSM of this invention is associated with the flexible lead FL within the right ventricle RV in spaced relationship to the stimulation electrode SE.

Figure 2:
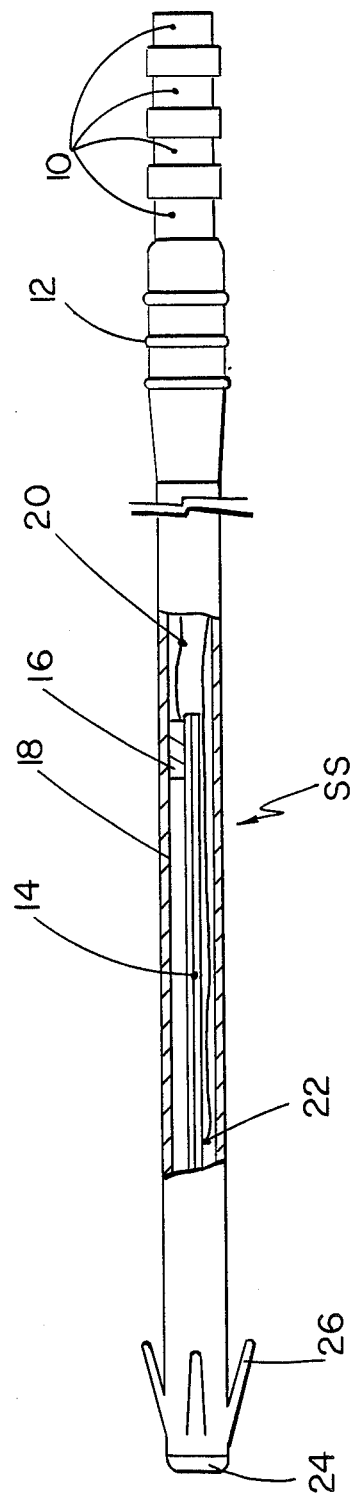
FIG. 2 is a view with parts in section of one embodiment of the invention.

A view of one embodiment of a sensing system SS, presenting its principal parts, is shown in FIG. 2. The first means comprises a conventional multipolar electrical connection 10 to the heart pacemaker system. The electrical connections may be either coaxial or in some other arrangement. The connections may be made out of any biocompatible electrically conducting material with biocompatible insulating medium used to separate the various poles. Conventional sealing mechanisms 12 maintain a barrier between the electrical connections 10 and the conductive fluids of the body. A self-contained, self-powered, flexible, electrical signal generating sensing means 14 is mounted for cantilever action on a fixed support 16 secured to the wall of a continuous flexible tube 18 which comprises a portion of the flexible lead FL in this embodiment. Details of the sensing means are described below. Electrically conducting lead lines 20 and 22 are connected to the sensing means 14 so as to conduct electric signals generated by the sensing means 14 to a heart pacemaker system HPS. The stimulation electrode 24 of the heart pacemaker system is positioned using a plurality of tines 26 which are attached in a conventional manner to heart tissue so as to fix the stimulation electrode 24 in position. The continuous flexible tube 18 is formed from a biocompatible, fatigue resistant, insulation material such as a silicon rubber, teflon or polyurethane.

Figure 3:
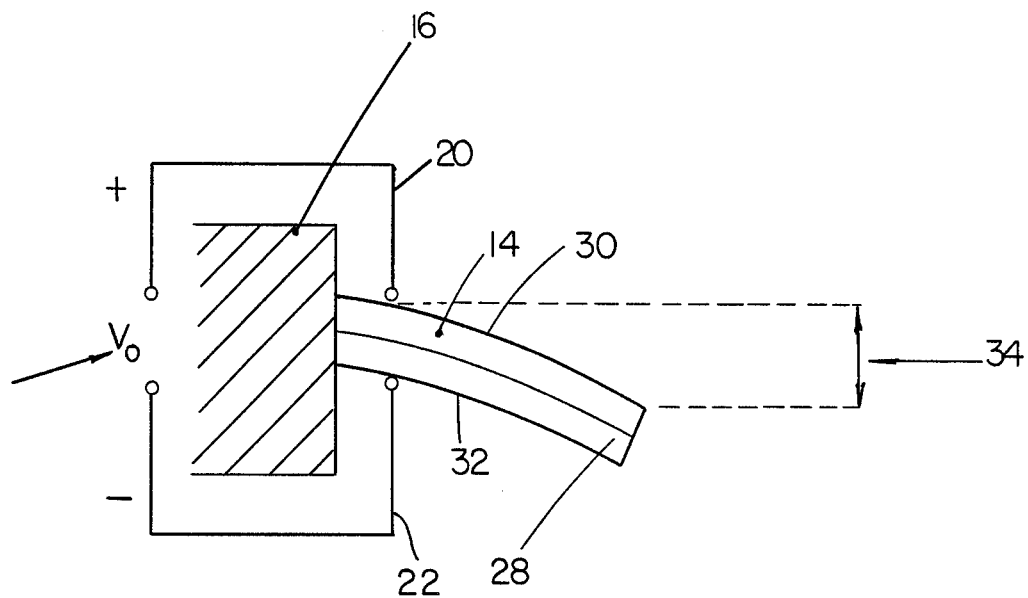
FIG. 3 is an illustration of the operation of a piezoelectric means.

In FIG. 3, there is schematically illustrated the electrical functioning of the sensing means 14 of one embodiment of this invention. A sensing means 14 is mounted on a fixed support 16 in a cantilever mode so that it may be delfected as illustrated by the end 28 thereof. Electrically conducting lead lines 20 and 22 are connected by suitable means to surfaces 30 and 32 of the sensing means 14. As illustrated in FIG. 3, the end 28 has been deflected from its original location, the dashed lines of FIG. 3, in an amount illustrated by the two headed arrow 34. The deflection of the end 28 generates an electric voltage Vo which is transmitted, in a preferred embodiment of the invention, through an electrical circuit to the heart pacemaker system.

The preferred embodiments of this invention use flexible piezoelectric polymer films. Flexible piezoelectric polymers are now readily available from vendors such as the Penwalt Corporation in the United States of America and sold under the trade name "Kynar". The polymers are available in a variety of shapes, thicknesses, metallizations and factory supplied wire bonding pads. The most common type of commercially available piezoelectric polymers consist of poly (vinylidene fluoride) (PVDF), processed by a combination of heat, pressure (drawing out of material) and exposure to strong electric fields. Composite type PVDF polymers are also being developed which incorporate powdered lead—zirconate—titanate (PZT) and also PZT powder incorporated in some other polymer matrix such as epoxy resin. In this invention PVDF has been utilized in the sensing system as the sensing means to detect displacement within the heart caused by hemodynamic changes.

The theory to calculate the electrical output available from piezoelectric devices is well established and is available from a number of sources. In terms of the proposed device a number of relevant factors are discussed below.

The output available from a PVDF sensor increases according to a number of factors. As the thickness of a PVDF film decreases, the output increases, however, as the film becomes very thin, it becomes difficult to fabricate. The problem of maximizing the output can be solved by constructing a "bimorph", or if required, a multimorph sandwiched construction. The properties of such a construction are such that as the thickness of the sandwich increases, so does the electrical output. Also the electrical output increases as a function of the inverse of the length of the sandwich, for a cantilever mode of bending.

A piezo film laminate as proposed in one embodiment of the sensing means can be modelled for a layout, such as that illustrated in FIG. 3, as follows:

$$V = \tfrac{3}{4}(g_{31} Y t^2 / L^2) x$$

where:
V = Voltage output
$g_{31}$ = piezoelectric voltage or strain constant
Y = Young's modulus
t = thickness of bimorph
L = length of bimorph
x = amount of deflection Further information related to this model can be found in the "Kynar Piezo Film Technical Manual" by Penwalt Corporation, the disclosure of which is incorporated herein by reference.

Figure 4:
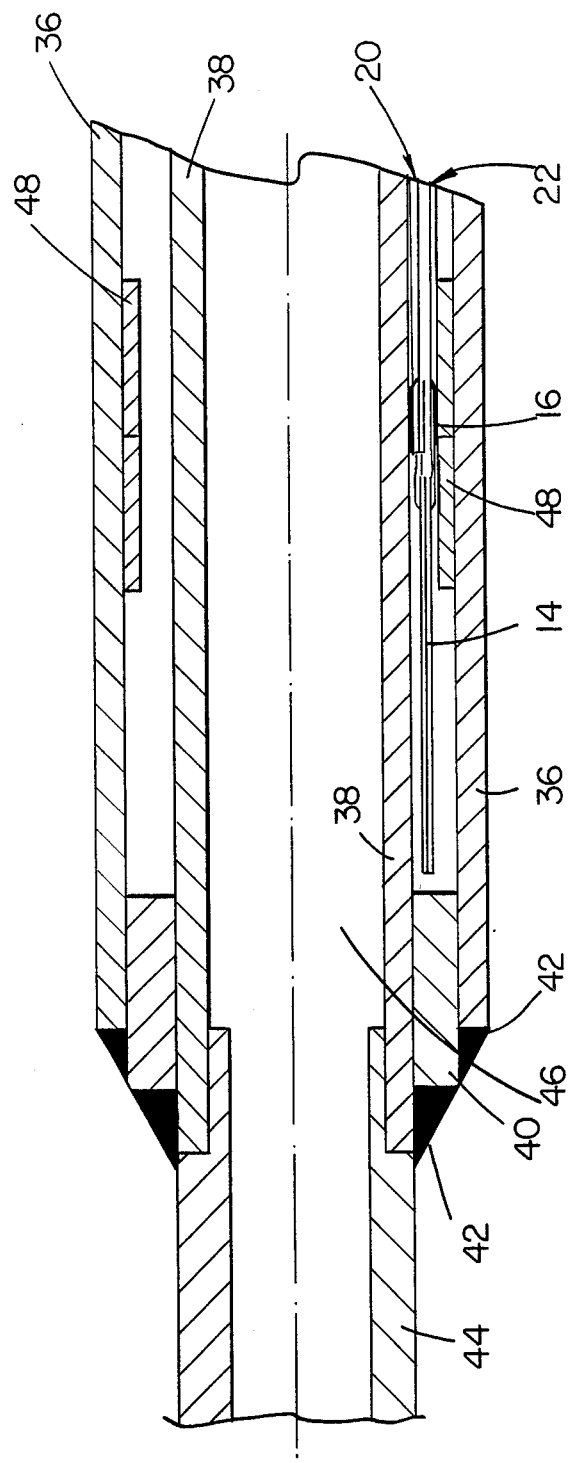
FIG. 4 is a schematic illustration of a portion of another embodiment of the invention.

The embodiment of the invention illustrated in FIG. 4 comprises a flexible outer tube 36 and a flexible inner tube 38 joined together through a member 40 by suitable means, such as welds or adhesive 42, a portion of which which also joins the inner flexible tube 38 to another flexible tube 44. The end of the flexible tube 44 (not shown) may be secured to an implanted medical device. The interior 46 of the flexible tubes 38 and 44 may be used as desired. A sensing means 14 is located between the outer flexible tube 36 and the inner flexible tube 38. A rigid member 48 is secured to the outer flexible tube 36 so as to provide a relatively fixed support for the fixed support 16 which is secured thereto. A displacement of the flexible tubes 36 and 38 will cause a deflection of the sensing means 14 so as to generate a voltage which is transmitted as desired by the electrically conducting lead lines 20 and 22.

Figure 5:
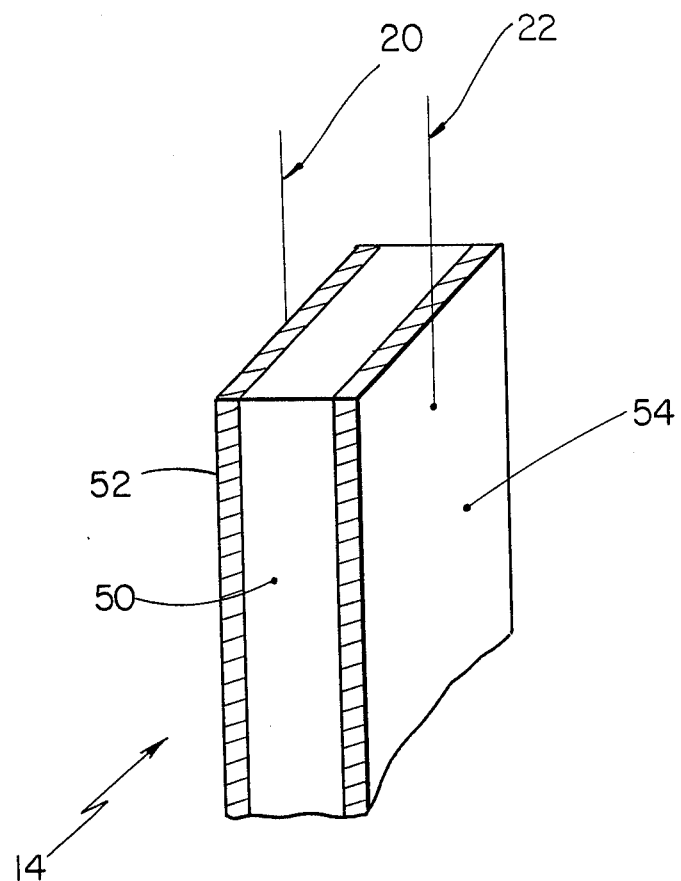
FIG. 5 is a view of a portion of a single strip of piezoelectric film.

The construction of one embodiment of a sensing means 14 is illustrated in FIG. 5 and comprises a thin film 50, usually in micron sizes, of poly (vinylidene fluoride) which has been specially processed so as to have electrical energy generating surfaces 52 and 54 when subjected to forces bending the film 50. The film 50 can be in strip form of any desired length and width but preferably has a longitudinal extent substantially greater than its lateral extent. Electrically conducting lead lines 20 and 22 are electrically connected to the surfaces 52 and 54 and are used to transmit the electrical energy generated by the surfaces 52 and 54.

Figure 6:
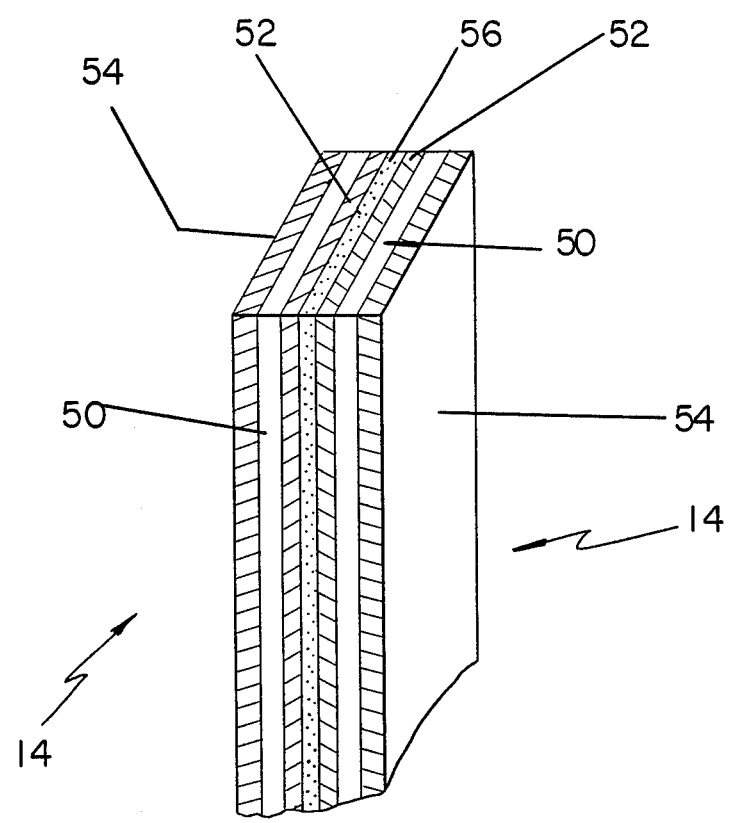
FIG. 6 is a pictorial view of a portion of piezoelectric bimorph.

In FIG. 6, there is illustrated another embodiment of a sensing means 14 which comprises a lamination of two of the sensing means 14, illustrated in FIG. 5, laminated together. An adhesive 56 is used to bond the adjacent surfaces of the sensing elements 14 together. The adhesive 56 provides an electrical connection between the adjacent surfaces of the sensing means 14. The adhesive used must be tough, fatigue resistant, mositure resistant, biocompatible and resistant to peel and shear forces. Adhesives which have been found to be suitable are cyanoacrylates and acrylics, particularly the toughened varieties. The sensing means 14, as illustrated in FIG. 6, is known as a bimorph. The connection illustrated in FIG. 6 is a series connection. Two lead lines (not shown) similar to electrically conducting lead lines 20 and 22 are used to transmit the generated electrical signal.

Figure 7:
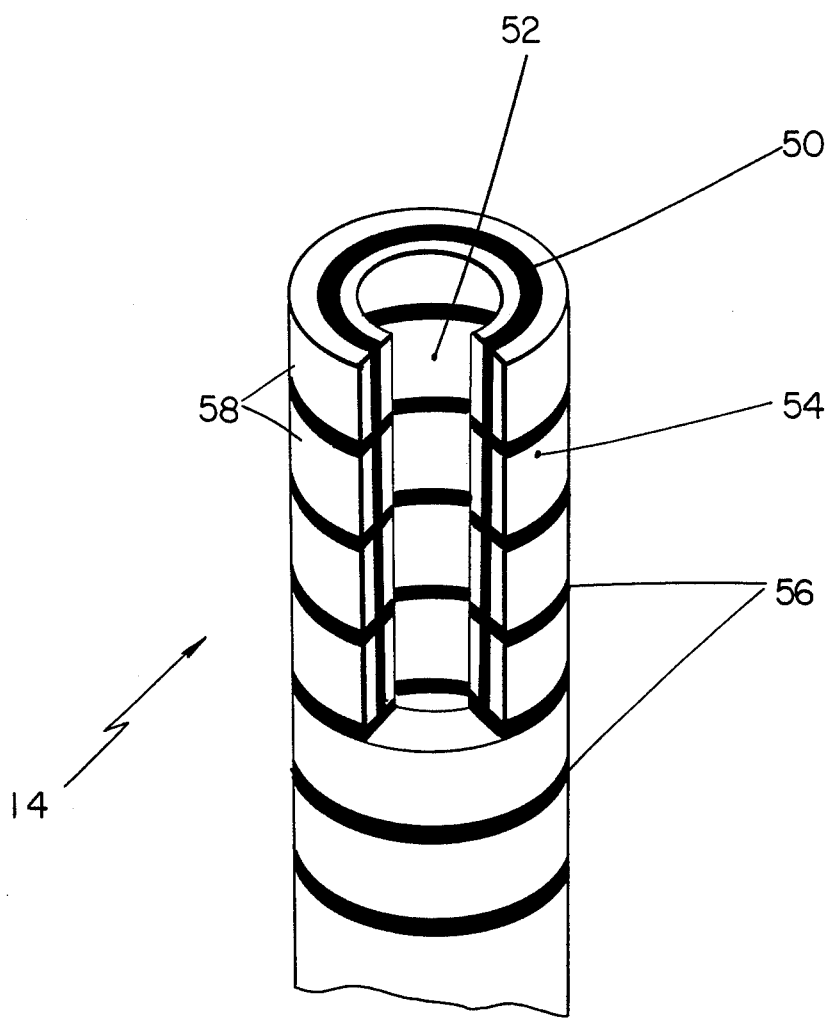
FIG. 7 is a pictorial view of a laminated tube type sensing means.

In the embodiment illustrated in FIG. 7, the sensing means 14 comprises a laminate of a plurality of sensing means 58, each comprising a ring shaped film 50 having electrical energy generating surfaces 52 and 54. The sensing means 58 are laminated together by adhesive 56.

Figure 8:
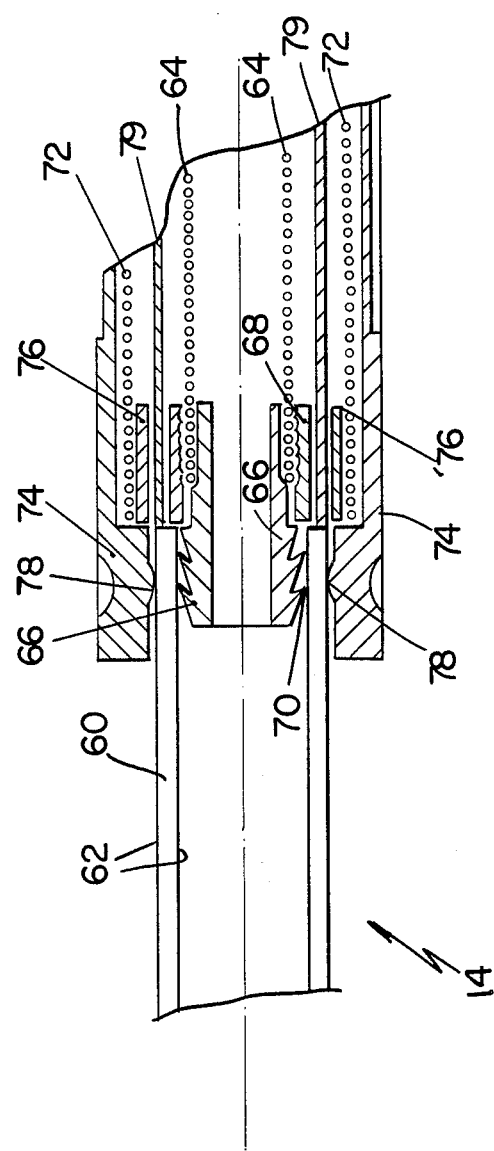
FIG. 8 is a view with parts in section of a portion of a sensing system using a tube type sensing means.
Figure 8A:
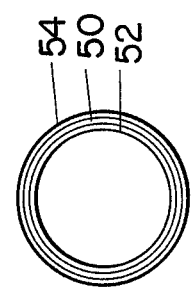
FIG. 8a is an end view of the tube type sensing means of FIG. 8.

The sensing means 14 in the embodiment illustrated in FIG. 8 comprises an elongated, flexible tube 60, constructed as described above using a film 50 in tubular form, FIG. 8a, with electrical energy generating inner and outer surfaces 52 and 54. The inner and outer surfaces 52 and 54 of the flexible tube 60 are coated with an electrically conducting compound 62. In FIG. 8, the electrically conducting lead line corresponding to electrically conducting lead line 20 of FIG. 5 comprises an electrically conducting helix 64 that is electrically secured to an electrical connector 66 by a conventional swaging device 68. The electrical connector 66 has a plurality of barbs 70 that provide the electrical connection between the inner surface 52 of the flexible tube 60 and the helix 64. In FIG. 8, the electrically conducting lead line corresponding to electrically conducting lead line 22 of FIG. 5 comprises an electrically conducting helix 72 that is electrically secured to an electrical connector 74 by a conventional swaging device 76. The electrical connector 74 has an annular inwardly directed projection 78 that provides the electrical connection between the outer surface 54 of the flexible tube 60 and the helix 72. An inslating tube 79 electrically separates the helix 64 from the helix 72. The flexible tube 60 should not be of totally uniform thickness. This can be accomplished by running one or more grooves (not shown) along the length of each of the outer and inner surfaces of the flexible tube 60.

The sensing system in the embodiment in FIGS. 9 and 9a is similar in many respects to the embodiment of FIG. 4. The sensing means 14 is located between the outer flexible tube 36 and the inner flexible tube 38. The ends of the flexible tubes 36 and 38 are joined to a housing 80 comprising a portion of a heart pacemaker implant. The stimulation electrode 24 and the tines 26 are the same as in FIG. 2. The coil 82 transmits a signal from the heart pacemaker system to cause the mechanism 84 to function to cause the stimulation electrode 24 to stimulate the heart. The sensing means 14, as illustrated in FIG. 9a, is a bimorph, as described above in relation to FIG. 6, comprising two sensing means 14 joined together by the adhesive 56. If desired, an electrical insulator 85 is positioned between the upper portions of the sensing means 14. A pair of fixed supports 16 are used to provide the cantilever mounting for the sensing means 14. The fixed supports are in frictional engagement with the adjacent surfaces of the outer tube 36 and the inner tube 38.

Figure 10:
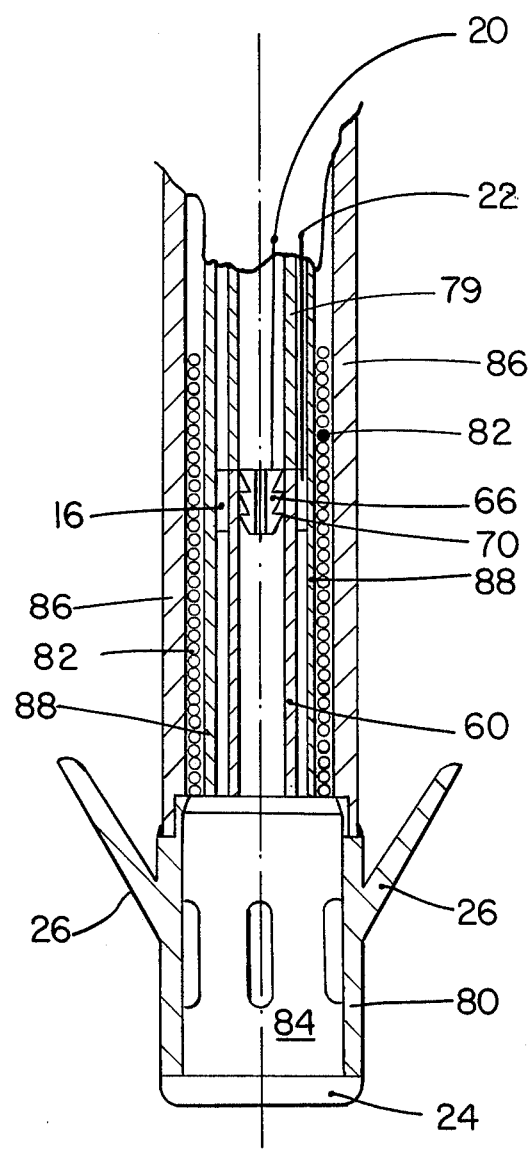
FIG. 10 is a view with parts in section of a portion of another sensing system and a tip of a heart pacemaker.

The sensing system in the embodiment illustrated in FIG. 10 is similar in many respects to the embodiment illustrated in FIG. 8. The sensing means comprises the flexible tube 60 and is associated with a heart pacemaker implant system similar to that in FIG. 9. The coil 82 is located between an outer flexible tube 86 and an inner flexible tube 88. The fixed support 16 is in frictional engagement with the inner surface of the flexible tube 88 and provides the cantilever mounting for the flexible tube 60. The electrical connector 66 has barbs 70 in electrical contact with the inner surface of the flexible tube 60 and transmits a generated electric signal over electrically conducting the lead line 20. The lead electrically conducting lead line 22 is used to transmit an electric signal generated by the outer surface of the flexible tube 60. An insulating tube 79 electrically separates the lead line 20 from the lead line 22.

Figure 11:
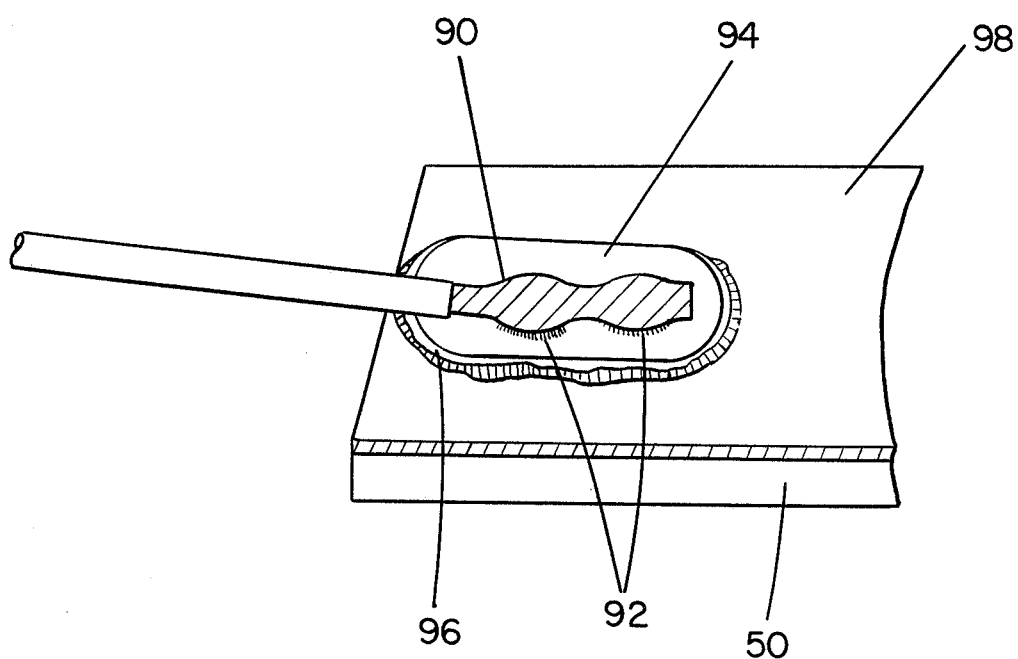
FIG. 11 is a pictorial view of a weld joint of a lead line to a sensing means.

Electrical connections may be made to the piezoelectric polymer by means of thin metal pads to which are attached the electric wires and the polymer. Such an arrangement is presented in FIG. 11 where an insulated, braided wire 90 is bonded by welding 92, or by means of a conductive adhesive, to a conductive thin metal pad 94 which is in turn bonded by conductive adhesive 96 to a conducting coating 98 of a piezoelectric polymer substrate 50.

Figure 12:
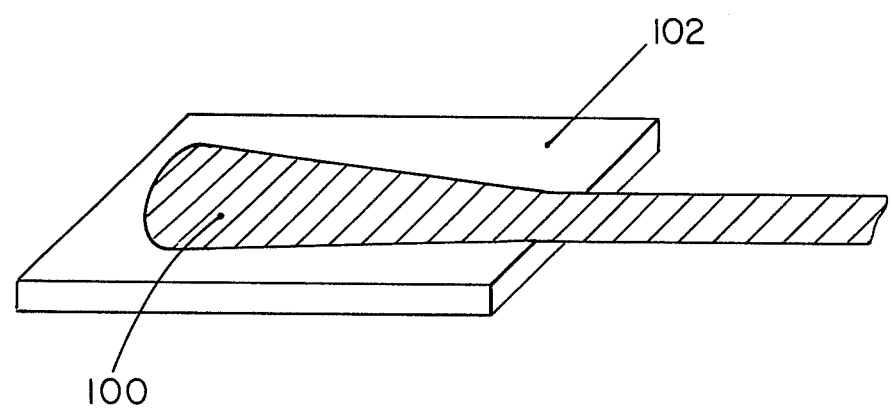
FIG. 12 is a pictorial view of another joint between a lead line and a sensing means.

Other methods for making electrical connections to the polymer include (but are not limited to) the use of a polymeric conductor 100 attached directly to the piezolectric substrate 102 as illustrated in FIG. 12.

Figures 13, 13A:
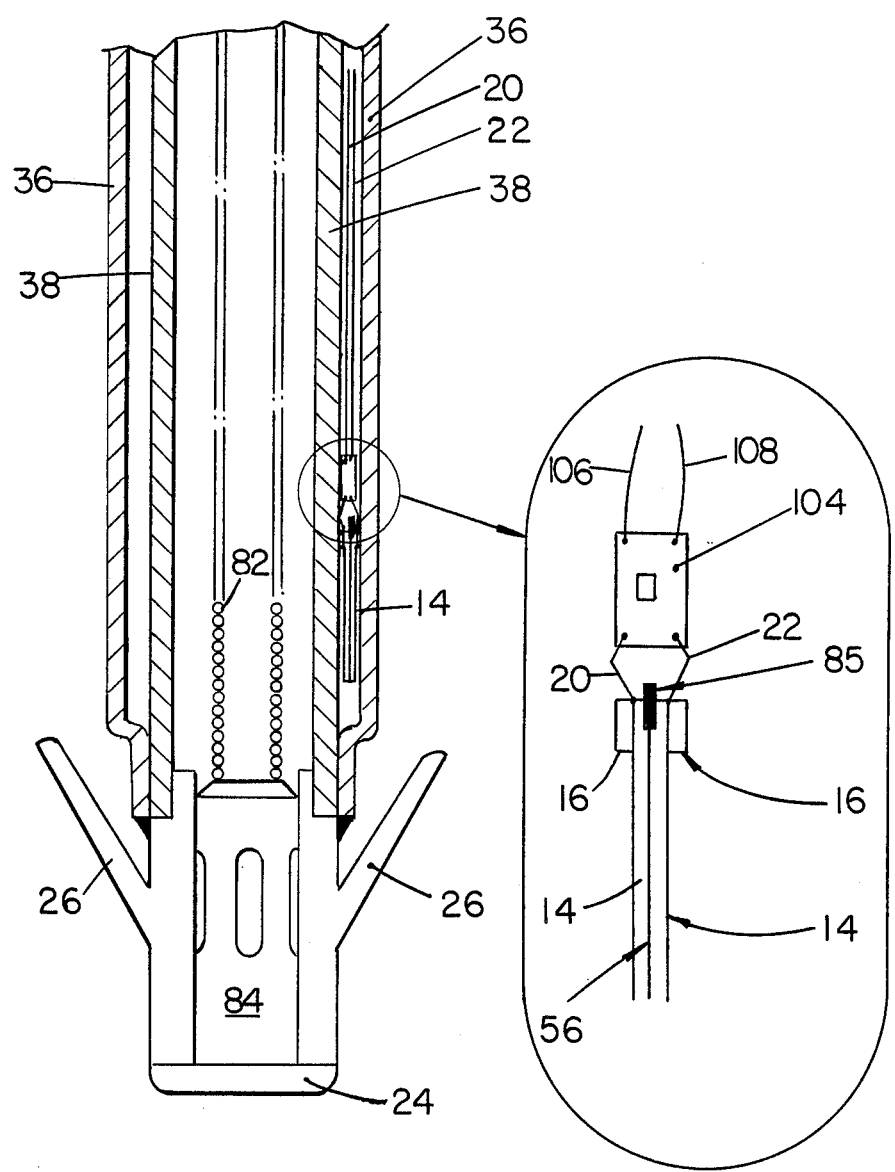
FIG. 13 is a view with parts in section of a portion of another sensing system and a tip of a heart pacemaker.
FIG. 13a is an enlargement of a portion of the circled area of FIG. 13.

The embodiment illustrated in FIGS. 13 and 13a is very similar to that in FIGS. 9 and 9a, but includes an electronics package 104 connected to the electrically conducting lead lines 20 and 22 to pre-process the signal from the sensing means 14 and produce a new electric control signal. Electrically conducting lead lines 106 and 108 transmit the new electrical control signal to the electronic control circuit ECC.

Figure 14:
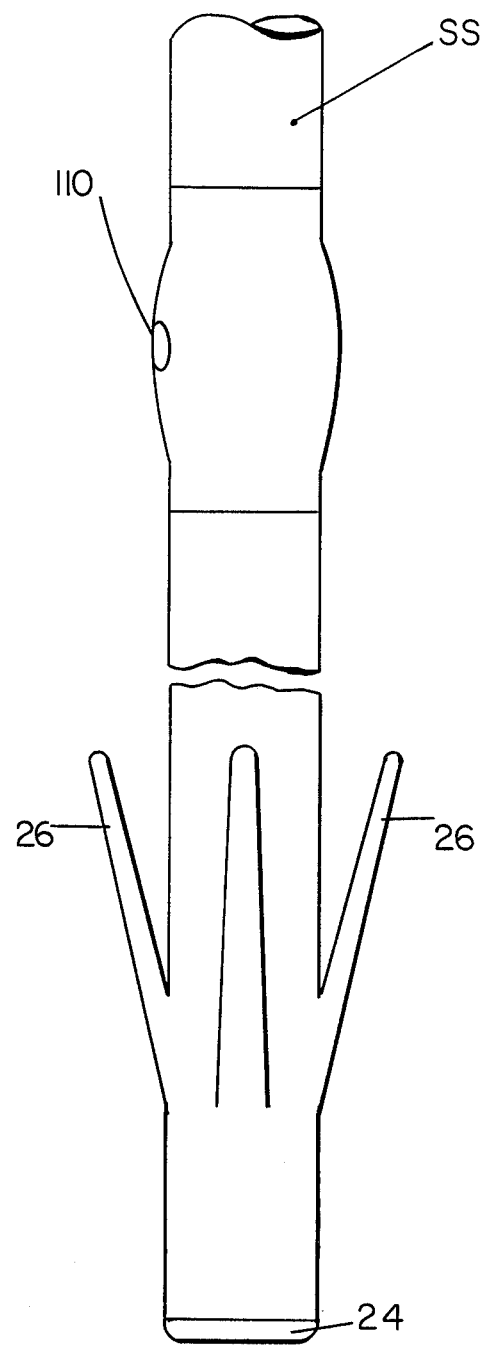
FIG. 14 is a view of a portion of another sensing system showing a window for a monitoring device.

It may be possible to drive information on pressure from the sensing system by a mathematical analysis of the output of the sensing means. However, it is also possible to include a pressure transducer or a transducer to measure other physical or chemical parameters in the sensing system SS as shown in FIG. 14. The opening 110 for a sensor window for detecting pressure is incorporated as part of the sensing system.

Figure 15:
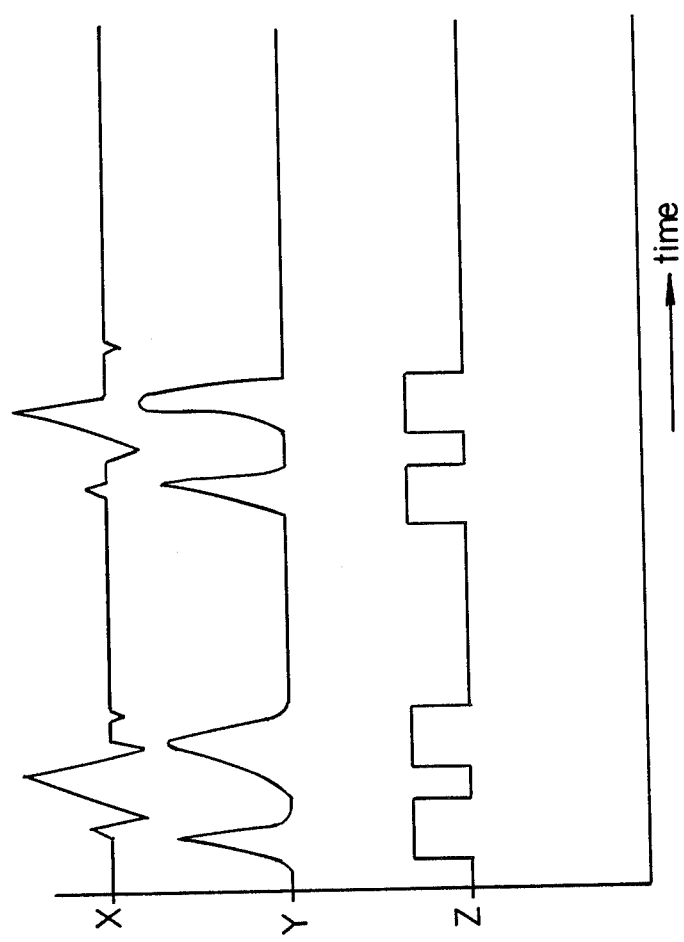
FIG. 15 is a typical output of the sensing system according to this invention.

A hemodynamic sensing system constructed according to the present invention (as shown in FIG. 9) was implanted in the right ventricle of the heart of a sheep. A typical output of the device in shown in FIG. 15. The ECG waveform (X) is represented by its mechanical equivalent and (Y) is the output of the hemodynamic sensing system. It can be seen that the output of a sensing system gives an indication of the hemodynamic state of the heart showing a good correspondence with the ECG waveform. This data may be digitized in a number of ways, one of which is presented in (Z). Such variables as pulse width, height and rate can all be analyzed and translated into data such as stroke volume, type of heart activity, heart rate, capture verification for threshold tracking etc. The hemodynamic sensing system may be inserted by a transvenous insertion as described in an article on pages 62–64 of the Journal of the American Medical Association, Jan. 4, 1980, Volume 243, which is incorporated herein by reference.

Figure 16:
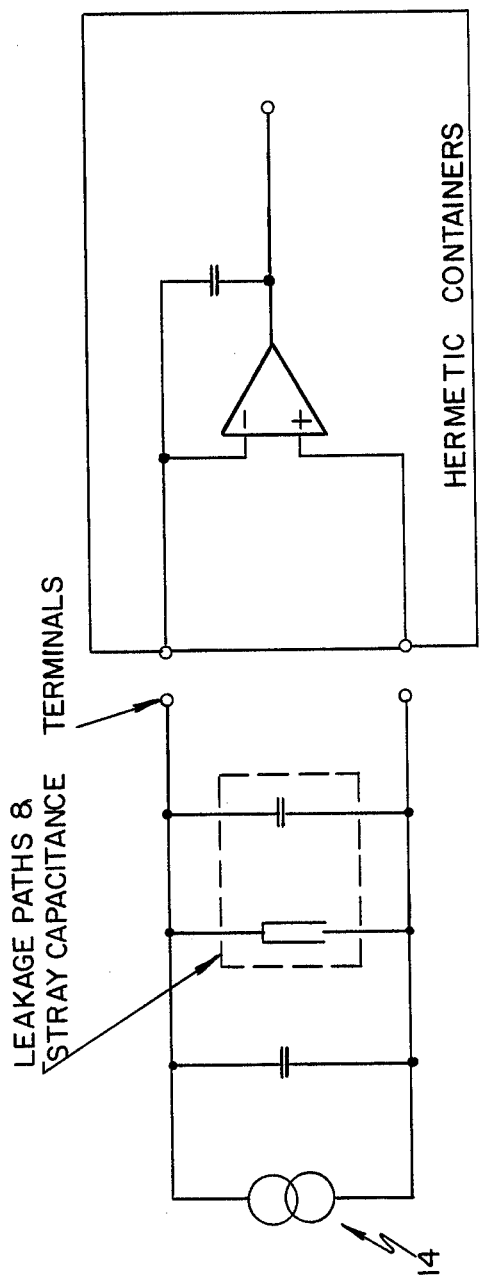
FIG. 16 is a diagram of a circuit for use in this invention.

FIG. 16 shows a charge amplifier configuration which maintains the input terminals at an extremely small voltage so that a negligible current flows in any leakage path. This is used to reduce voltage excursion across the piezoelectric sensing means 14. This reduces the effect of leakage paths and stray capacitance across the piezoelectric sensing means. The operation of this circuit is to transfer the charge generated on the piezoelectric sensing means to the feedback capacitor of the charge amplifier, while maintaining the input terminal voltage at zero. The resulting electrical signal is then fed through an electrically conducting lead system to the implanted medical device. Within the implanted medical device, the signal is recovered and used by the implanted medical device.

Any material in which some electrically measurable property reversibly changes as a function of strain on the material is suitable in a sensing means of this kind. Another possible material is a piezoresistive material such as some types of metallic glass which change their resistance as a function of the degree of deformation. Alternatively piezoresistive films can be constructed by metal deposition on suitable polymeric or metallic substrate by chemical vapour deposition or ion beam etching to result in the desired properties. These are regarded to fall within the scope of the present invention.

It is contemplated that the inventive concepts herein described may be variously otherwise embodied and it is intended that the appended claims be construed to include alternative embodiments of the invention except insofar as limited by the prior art.

What is claimed is:

1. An implantable medical system for use in the control of the operation of a part of a body comprising:
   control unit means for mounting in one location of a body;
   control circuit means in said control unit means for controlling the operation of the control unit means;
   battery means in said control unit means for supplying electrical energy to said control unit means and said control circuit means;
   flexible lead means for mounting in said body and being connected to said control unit means and extending from said control unit means to another location inside said body;
   said flexible lead means comprising a continuous flexible hollow tube having an outer and an inner surface;
   stimulation electrode means mounted on said flexible lead means and being located in said another location for receiving electrical energy from said control unit means through said flexible lead means and applying electrical energy to said body at said another location;
   self-contained, self-powered, flexible, electrical signal generating means mounted in a portion of said flexible lead means in spaced relationship to said stimulation electrode means for self-generation of electrical control signals solely by mechanical movement induced solely by flexible movement of said flexible lead means in said another location caused by action of and conditions in the body and without any electrical connection to and supply of electrical energy from any other source;

a fixed support secured to said inner surface;

said self-contained, self-powered, flexible, electrical signal generating means mounted for cantilever action on said fixed support; and electrical control signal transmitting means, connected to said self-contained, self-powered, flexible, electrical signal generating means and said control circuit means, to transmit the generated electrical control signals to said control circuit means.

2. A system as in claim 1 wherein said self-contained, self-powered, flexible, electrical signal generating means comprises:

at least one shaped article formed from a piezoelectric material.

3. A system as in claim 2 wherein said piezoelectric material comprises:

a polymeric piezoelectric film.

4. A system as in claim 3 wherein:

said polymeric piezoelectric film is formed using poly (vinylidene fluoride).

5. A system as in claim 3 wherein said polymeric piezoelectric film comprises:

a rectangular strip having a longitudinal extent substantially greater than its lateral extent.

6. A system as in claim 2 wherein said piezoelectric material comprises:

a length of polymeric piezoelectric film in tubular form.

7. A system as in claim 1 wherein said self-contained, self-powered, flexible, electrical signal generating means comprises:

a laminate of a plurality of piezoelectric films.

8. A system as in claim 1 wherein said implanted medical device comprises:

a heart pacemaker system wherein said stimulation electrode means is attached to heart tissue at the apex of the right ventricle of the heart.

9. A system as in claim 8 wherein:

said continuous flexible hollow tube extending from the superior vena cava through the right auricle and into the right ventricle to said stimulation electrode means.

10. A system as in claim 9 and further comprising:

a second continuous flexible tube means surrounding said first continuous flexible tube means in sealed relationship thereto; and said self-contained, self-powered, flexible, electrical signal generating means encased between said first and second continuous flexible tube means in said right ventricle in spaced relationship to said stimulation electrode means.

11. A system as in claim 9 wherein said self-contained, self-powered, flexible, electrical signal generating means comprises:

a polymeric piezoelectric film.

12. A system as in claim 10 and further comprising:

a substantially rigid annular member secured to the inner surface of said second continuous flexible tube means within said right ventricle;

means for supporting said polymeric piezoelectric film on said substantially rigid annular member; and said polymeric piezoelectric film being located between said substantially rigid annular member and staid stimulation electrode means.

13. A system as in claim 12 and further comprising:

first electrically conducting lead means located between said first and second continuous flexible tube means;

said first electrically conducting lead means extending between and connected to said polymeric piezoelectric film and said control circuit means to transmit said electrical control signals generated by said polymeric piezoelectric film to said control circuit means.

14. A system as in claim 13 and further comprising:

second electrically conducting lead means located within said first continuous flexible tube means; and said second electrically conducting lead means extending between and connected to said control unit means and said stimulation electrode means to transmit an electrical signal from said control unit means to said stimulation electrode means to stimulate said heart.

15. A system as in claim 8 wherein said self-contained, self-powered, flexible, electrical signal generating means comprises:

a tubular polymeric piezoelectric film having an outer and an inner surface;

a first electrical conductor electrically connected to said outer surface of said tubular polymeric piezoelectric film;

a second electrical conductor electrically connected to said inner surface of said tubular polymeric piezoelectrical film; and first electrically conducting lead means extending between and connected to said first and second electrical conductors and said control circuit means to transmit electrical signals generated by said tubular polymeric piezoelectric film to said control circuit means.

16. A system as in claim 15 wherein:

said second electrical conductor has a plurality of barbs in electrical contact with said inner surface; and said first electrically conducting lead means is in the form of helices.

17. A system as in claim 16 wherein said flexible lead means includes:

a first continuous flexible tube means extending from the superior vena cava through the right auricle and into the right ventricle to said stimulation electrode means;

a second continuous flexible tube means located within and concentric to said first continuous flexible tube means;

second electrically conducting lead means located between said first and second continuous flexible tube means;

said second electrically conducting lead means extending between and connected to said control unit means and said stimulation electrode means to transmit an electrical signal from said control unit means to said stimulation electrode means to stimulate said heart; and said self-contained, self-powered, flexible, electrical signal generating means located within said second continuous flexible tube means in said right ventricle in spaced relationship to said stimulation electrode means.

18. A system as in claim 17 and further comprising:

said first electrical conductor is attached to the inner surface of said second continuous flexible tube means; and said tubular polymeric piezoelectric film is located between said first electrical conductor and said stimulation electrode means.

19. A system as in claim 8 and further comprising:

a first continuous flexible tube means, comprising a portion of said flexible lead means, extending from the superior vena cava through the right auricle and into the right ventricle to said stimulation electrode means;

a second continuous flexible tube means surrounding said first continuous flexible tube in sealed relationship thereto;

said self-contained, self-powered, flexible, electrical signal generating means encased between said first and second continuous flexible tube means in said right ventricle in spaced relationship to said stimulation electrode means;

said self-contained, self-powered, flexible, electrical signal generating means comprises a polymeric piezoelectric film;

support means for supporting said polymeric piezoelectric film, said support means secured to the inner surface of said second continuous flexible tube means; and said polymeric piezoelectric film located between said support means and said stimulation electrode means.

20. A system as in claim 19 and further comprising:

first electrically conducting lead means located between said first and second continuous flexible tubes;

said first electrically conducting lead means extending between and connected to said polymeric piezoelectric film and said control circuit means to transmit said electrical control signals generated by said polymeric piezoelectric film to said control circuit means.

21. A system as in claim 20 and further comprising:

second electrically conducting lead means located within said first continuous flexible tube means;

said second electrically conducting lead means extending between and connected to said control unit means and said stimulation electrode means to transmit an electrical signal from said control unit means to said stimulation electrode means to stimulate said heart.

22. A system as in claim 21 and further comprising:

an electronic circuit means located between said first and second continuous flexible tube means in a portion thereof located in said right ventricle for providing an electric function on said electrical signal generated by said polymeric piezoelectric film;

said first electrically conducting lead means extending between and connected to said polymeric piezoelectric film and said electronic circuit means to transmit said electric means control signals generated by said piezoelectric film to said electronic circuit means;

said electronic circuit means producing a new electric control signal;

third electrically conducting lead means located between said first and second continuous flexible tube means; and said third electrically conducting lead means extending between and connected to said electronic circuit means and said control circuit means to transmit said new electrical control signal produced by said electronic circuit means to said control circuit means.

23. A system as in claim 22 and further comprising:

means for electrically connecting one end of said first electrically conducting lead means to said polymeric piezoelectric film and comprising;

a thin metal pad bonded to said one end by an electrically conducting weld; and said thin metal pad bonded to a portion of the surface of said polymeric piezoelectric film by an electrically conducting adhesive.

24. A system as in claim 1 and further comprising electrical conducting connecting means for connecting said electrical control signal transmitting means to said self-contained, self-powered, flexible electrical signal generating means.

25. A system as in claim 24 wherein said electrical conducting means comprises:

a thin metal pad bonded to said electrical control signal transmitting means by an electrically conducting weld; and said thin metal pad bonded to a portion of said self-contained, self-powered, flexible electrical signal generating means.

26. A system as in claim 25 wherein said self-contained, self-powered, flexible electrical signal generating means comprises:

a polymeric piezoelectric film.

27. A method for controlling the operation of an implanted medical system for use in the control of the operation of a part of a body comprising:

implanting portions of a medical system at spaced apart locations in a body;

locating at one location in a body a control unit means having a control circuit means for controlling the operation of said control unit means and a battery means for supplying electrical energy to said control unit means and said control circuit means;

locating a stimulation electrode means at another location in said body;

connecting flexible lead means comprises a continuous flexible hollow tube having an outer and an inner surface to said control unit means and to said stimulation electrode means;

transmitting an electrical signal from said control unit means to said stimulation electrode means through said flexible lead means so that said stimulation electrode means will stimulate movement at said another location in said body;

locating a self-contained, self-powered, flexible, electrical control signal generating means in a portion of said flexible lead means in spaced relationship to said stimulation electrode means;

mounting said self-contained, self-powered, flexible, electrical signal generating means on said inner surface for cantilever action;

flexing said self-contained, self-powered, flexible, electrical signal generating means to generate an electric signal solely by mechanic movement of said flexible lead means in said another location caused by action of and conditions in the body and without any electrical connection to or supply of electrical energy from any other source; and transmitting said electrical signal generated by said self-contained, self-powered, flexible, electrical signal generating means through said flexible lead means to said control circuit means.

28. A method as in claim 27 and further comprising:

implanting said stimulation electrode means in tissue at the apex of the right ventricle of a human heart.

* * * * *